US012616512B2

(12) United States Patent
Melnick et al.

(10) Patent No.: US 12,616,512 B2
(45) Date of Patent: May 5, 2026

(54) SURGICAL ROD CUTTER-BENDER ASSEMBLY

(71) Applicant: Symmetry Medical Manufacturing, Inc., Warsaw, IN (US)

(72) Inventors: Christopher Melnick, Milwaukee, WI (US); Tomas Fandel, Milwaukee, WI (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 552 days.

(21) Appl. No.: 17/890,084

(22) Filed: Aug. 17, 2022

(65) Prior Publication Data

US 2024/0058046 A1     Feb. 22, 2024

(51) Int. Cl.
    *A61B 17/88*          (2006.01)
    *A61B 17/56*          (2006.01)

(52) U.S. Cl.
    CPC .... *A61B 17/8863* (2013.01); *A61B 2017/564* (2013.01)

(58) Field of Classification Search
    CPC ...................... A61B 17/8863; A61B 2017/564
    See application file for complete search history.

(56) References Cited

U.S. PATENT DOCUMENTS

| | | | | |
|---|---|---|---|---|
| 515,799 | A * | 3/1894 | Smith ...................... | B25B 7/22 |
| | | | | 7/131 |
| 3,716,879 | A | 2/1973 | Boyajian | |
| 4,033,388 | A | 7/1977 | Ruegger | |
| 4,104,752 | A | 8/1978 | Amrein et al. | |
| 5,084,935 | A * | 2/1992 | Kalthoff ................... | A61C 7/04 |
| | | | | 433/4 |
| 6,418,773 | B1 | 7/2002 | Tolman | |
| 6,497,133 | B1 | 12/2002 | Rose | |
| 9,872,716 | B2 | 1/2018 | Cordaro et al. | |
| 11,303,083 | B2 * | 4/2022 | Wollert .................... | B25B 7/22 |

OTHER PUBLICATIONS

Tabletop Rod Cutter, Item #5770, information taken from Tecomet, Inc. website at www.tecomet.com, Jun. 22, 2022 (4 pages).
Mahe Medical GmbH product brochure; Table Rod Cutter and Rod Bender; published at least by Jul. 22, 2022 (4 pages).

* cited by examiner

*Primary Examiner* — Sameh R Boles
(74) *Attorney, Agent, or Firm* — TAYLOR & EDELSTEIN, PC

(57) ABSTRACT

A surgical rod cutter-bender assembly includes: a first portion including a protrusion; and a second portion including a recess associated with the protrusion, the first portion and the second portion together defining a pivot axis such that the first portion and the second portion are configured for pivoting relative to one another about the pivot axis.

11 Claims, 15 Drawing Sheets

1650

1651

Providing a surgical rod
cutter-bender assembly.

1652

Pivoting the first and second
portions relative to one another.

SURGICAL ROD CUTTER-BENDER ASSEMBLY

BACKGROUND OF THE INVENTION

1. Field of the Invention

The present invention relates to medical devices, and, more particularly, to surgical rod cutter-bender assemblies.

2. Description of the Related Art

Surgical rod cutters are known that have either a handheld configuration or a tabletop configuration. With respect to either configuration, such rod cutters include a plurality of jaws coupled together at their distal ends, at least one of the jaws including at its distal end at least one cutting hole, which allows for easy insertion and proper positioning of the rod prior to cutting. Also known are assemblies which provide for both cutting and bending.

What is needed in the art is an improved surgical rod cutter-bender assembly that is efficient and cost-effective.

SUMMARY OF THE INVENTION

The present invention provides a surgical rod cutter-bender assembly that provides for both cutting and bending of a surgical rod, with the bending occurring by way of a protrusion and a recess of respective portions that pivot relative to one another.

The invention in one form is directed to a surgical rod cutter-bender assembly, including: a first portion including a protrusion; and a second portion including a recess associated with the protrusion, the first portion and the second portion together defining a pivot axis such that the first portion and the second portion are configured for pivoting relative to one another about the pivot axis.

The invention in another form is directed to a method of using a surgical rod cutter-bender assembly, the method including the steps of: providing that the surgical rod cutter-bender assembly includes a first portion and a second portion, the first portion including a protrusion, the second portion including a recess associated with the protrusion, the first portion and the second portion together defining a pivot axis; and pivoting the first portion and the second portion relative to one another about the pivot axis.

An advantage of the present invention is that it provides a single assembly that provides for both cutting and bending of surgical rods (2-for-1), thereby reducing the required number of instruments for a particular surgery. Further, advantageously, fewer instruments are needed to be fit within a surgical tray or system, and the weight of the overall tray or system is reduced.

Another advantage of the present invention is that it enables a surgeon to exert additional control when bending surgical rods, to ensure the best rod shape for a patient's specific anatomy.

Yet another advantage of the present invention is that it reduces the amount of effort required from the surgeon to bend the surgical rod. Conventionally, users have to exert significant effort, because of the hardness and stiffness that is inherent in the material that is used for surgical rods. The present invention significantly increases the user's mechanical advantage, thus reducing the effort required of the user.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
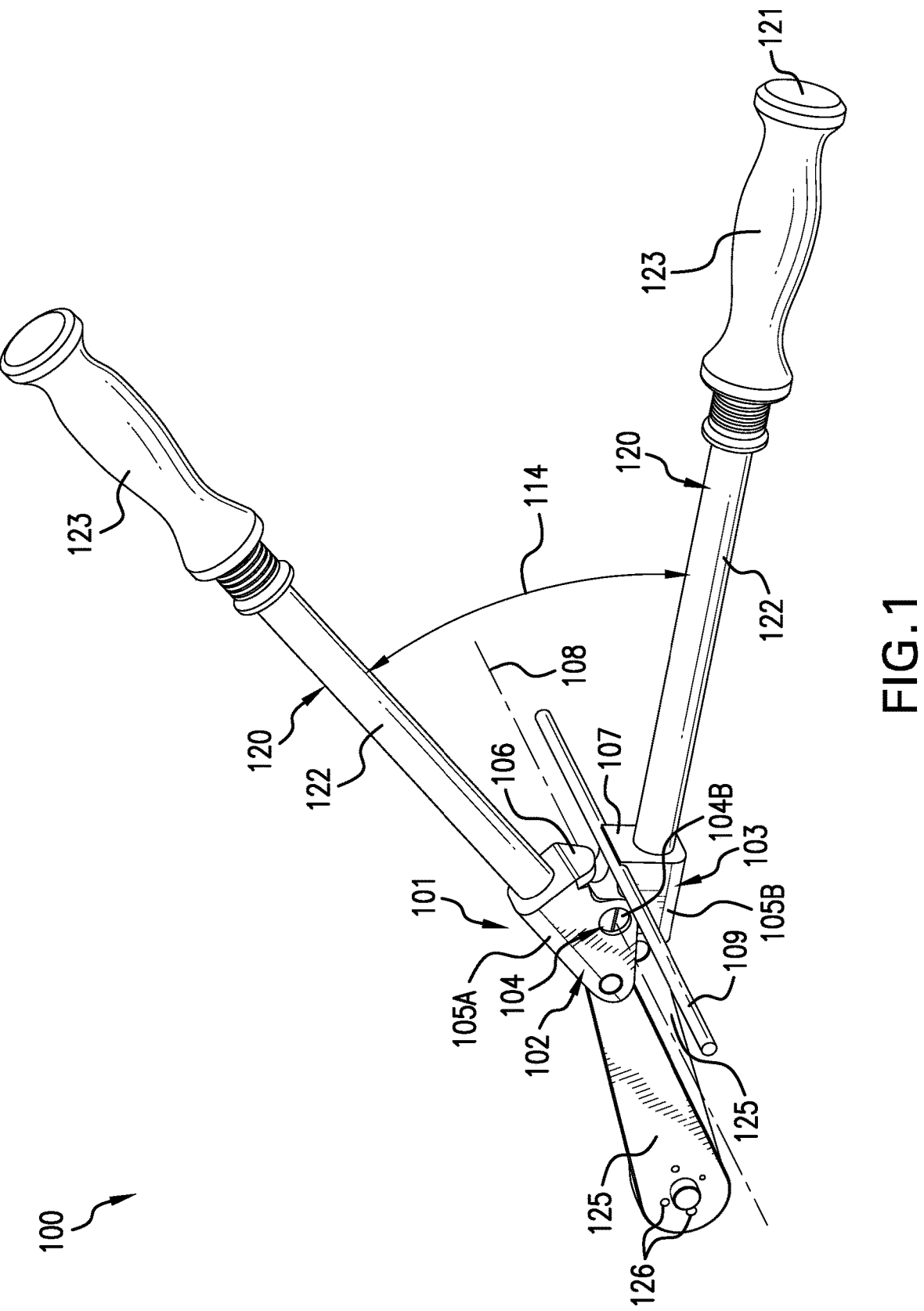
FIG. 1 is a perspective view of an exemplary embodiment of a surgical rod cutter-bender assembly, the surgical rod cutter-bender assembly including a pivot block assembly including a first portion and a second portion, the surgical rod cutter-bender assembly shown in an open position with a surgical rod in position to be bent by the surgical rod cutter-bender assembly, in accordance with an exemplary embodiment of the present invention.

Referring now to the drawings, and more particularly to FIG. 1, there is shown a surgical rod cutter-bender assembly 100 which generally includes a pivot block assembly 101, at least one handle 120, and a plurality of jaws 125. FIG. 1 (and associated FIGS. 2-7) show an exemplary embodiment of the present invention in a handheld configuration.

Pivot block assembly 101 includes a first portion 102, a second portion 103, and a fastener assembly 104 which couples first and second portions 102, 103 with one another. First and second portions 102, 103 can be made of any suitable material, for example and not by way of limitation, stainless steel, titanium, cobalt chromium (which can also be referred to as cobalt chrome), and/or a polymer, and portions 102, 103 can be made in any suitable manner. First portion 102 can be referred to as a male portion 102, and second portion 103 can be referred to as a female portion 103. First and second portions are pivotably coupled together by fastener assembly 104, which can be made of any suitable material and be any suitable type of fastener, for example, and not by way of limitation, a pivot pin 504A (FIG. 5) which receives (such as threadably) on an end thereof a cap or screw 104B to hold first and second portions 102, 103 together. Thus, first and second portions 102, 103, together with fastener assembly 104, define a pivot axis 108 such that first and second portions are configured for pivoting relative to one another about pivot axis 108, as indicated by double arrow 114 between handles 120 (because handles 120 are fixed to first and second portions respectively, movement of handles 120 toward or away from each other causes first and second portions 120, 103 to move correspondingly toward or away from each other). First and second portions 102, 103 each includes a base 105A, 105B, respectively. Base 105A of first portion 102 includes a protrusion 106, and base 105B of second portion 103 includes a recess 107 which is associated with protrusion 106. Such association of protrusion 106 and recess 107 is such that protrusion 106 and recess 107 are configured for bending a surgical rod 109 therebetween, and further such that recess 107 can be configured for at least partially receiving protrusion 106 therein, such as when surgical rod 109 is not positioned between and in contact with protrusion 106 and recess 107, though according to an embodiment of the present invention recess 107 can be configured for at least partially receiving protrusion 106 therein when surgical rod 109 is at least partially pressed into recess 107 by protrusion 106. According to an exemplary embodiment of the present invention, protrusion 106 and recess 107 are positioned at an interior portion of pivot block assembly 101 near a pivot area which includes pivot axis 108; stated another way, protrusion 106 and recess 107 are positioned proximally relative to pivot axis 108. Herein, proximal is viewed in reference to a free end 121 of the lower handle 120 (at the bottom right of FIG.

1); that is, what is most proximal is structure that is closest to free end 121. This reference is sufficient for a configuration of assembly 100 including a lower handle 120, which is a handheld configuration (first configuration). However, other configurations of the surgical rod cutter-bender assembly are also within the scope of the present invention; such configurations include: one that excludes lower handle 120, leaving a single handle 120 that is moved pivotably about pivot axis 108 to and from, for instance, a table top (such as where pivot block assembly 101 is fixed to a structure such as a table)(second configuration); or one that includes both upper and lower handles 120, but wherein lower handle 120 and/or pivot block assembly 101 is/are positioned within a device for immobilizing lower handle 120 and/or pivot block assembly 101 (third configuration). In the second configuration (omitting lower handle 120), proximal can be viewed in reference to the upper handle 120 (which is the only handle 120, as the lower handle 120 is omitted) when this upper handle 120 is fully at rest in its down position (such that protrusion 106 is on or in recess 107). An embodiment of the second version is shown below. In the third configuration, proximal is viewed as in the first configuration. The second and third configurations are deemed herein to be tabletop configurations. Thus, in any of these configurations, jaws 125 are positioned distally relative to pivot block assembly 101 (the present invention, however, also includes configurations wherein the jaws are positioned proximally relative to the pivot block assembly as well). In FIG. 1, recess 107 is shown with surgical rod 109 straight and resting atop a top portion of recess 107, with pivot block assembly 101 in an open position, wherein protrusion 106 is not engaging with surgical rod 109 or resting on or at least partially within recess 107 (conversely, a closed position of pivot block assembly 101 can occur when protrusion 106 has fully pressed surgical rod 109 within recess 107, or, alternatively, when protrusion 106, absent surgical rod 109, is resting on or in recess 107). Thus, in FIG. 1, surgical rod 109 has not yet been bent by assembly 100. Further, protrusion 106 and recess 107 are, according to an exemplary embodiment of the present invention, substantially parallel (within manufacturing tolerances) to pivot axis 108 and thus are situated transversely relative to a longitudinal extent of, for example, the lower handle 120 in FIG. 1; even so, the present invention also includes configurations wherein the protrusion and the recess are not substantially parallel relative to pivot axis (such as pivot axis 108) but are thus situated at an angle relative to the pivot axis. Surgical rod 109 can be made of, for example, or otherwise include stainless steel, titanium, and/or cobalt chromium (also referred to as cobalt chrome).

The at least one handle 120, in FIG. 1, is two handles 120, an upper handle 120 and a lower handle 120. Each of lower and upper handles 120 can include an elongate shaft 122 and a gripper portion 123, which can be connected to one another in any suitable manner, such as by way of a connection that includes a threaded connection, an interference fit, welding, and/or the like. Handles 120 can be made in any suitable manner. Shafts 122 can be made of any suitable material, for example and not by way of limitation, stainless steel, titanium, cobalt chromium, and/or a polymer. Lower handle 120 is coupled with second portion 103, and upper handle 120 is coupled with first portion 102, using any suitable connection, such as, for example and not limitation, by way of a connection that includes a threaded connection, an interference fit, welding, and/or the like. A surgeon can grasp handles 120 to open and close handles 120 relative to one another. Further, according to an exemplary embodiment of the present invention, handle(s) 120 can be telescoping to selectively provide even greater length to handle(s) 120 and thus greater mechanical advantage.

Jaws 125 are coupled (such as pivotably coupled) with pivot block assembly 101 at a proximal end of each respective jaw 125 and with one another at a distal end of each respective jaw 125, as is known. Further, at least one of jaws 125 includes at its distal end at least one cutting hole 126, which allows for easy insertion and proper positioning of rod 109 prior to cutting, as is known. Jaws 125 are configured for cutting surgical rod 109. How jaws 125 cut rod 109 is known and thus will not be explained further. Jaws 125 can be made in any suitable manner and of any suitable material, for example and not by way of limitation, stainless steel, titanium, and/or cobalt chromium.

Figure 2:
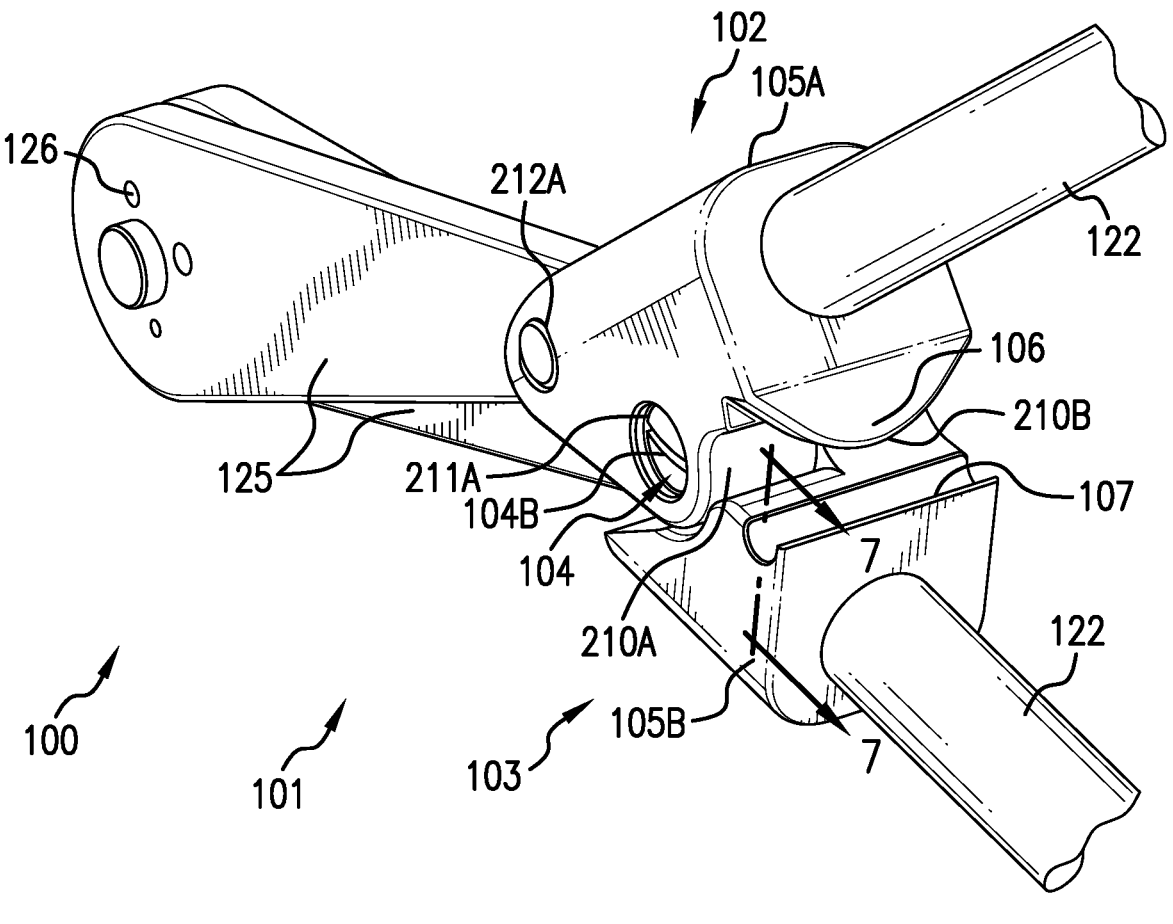
FIG. 2 is a perspective view of the surgical rod cutter-bender assembly of FIG. 1, with portions broken away and omitting the surgical rod.
Figure 5:
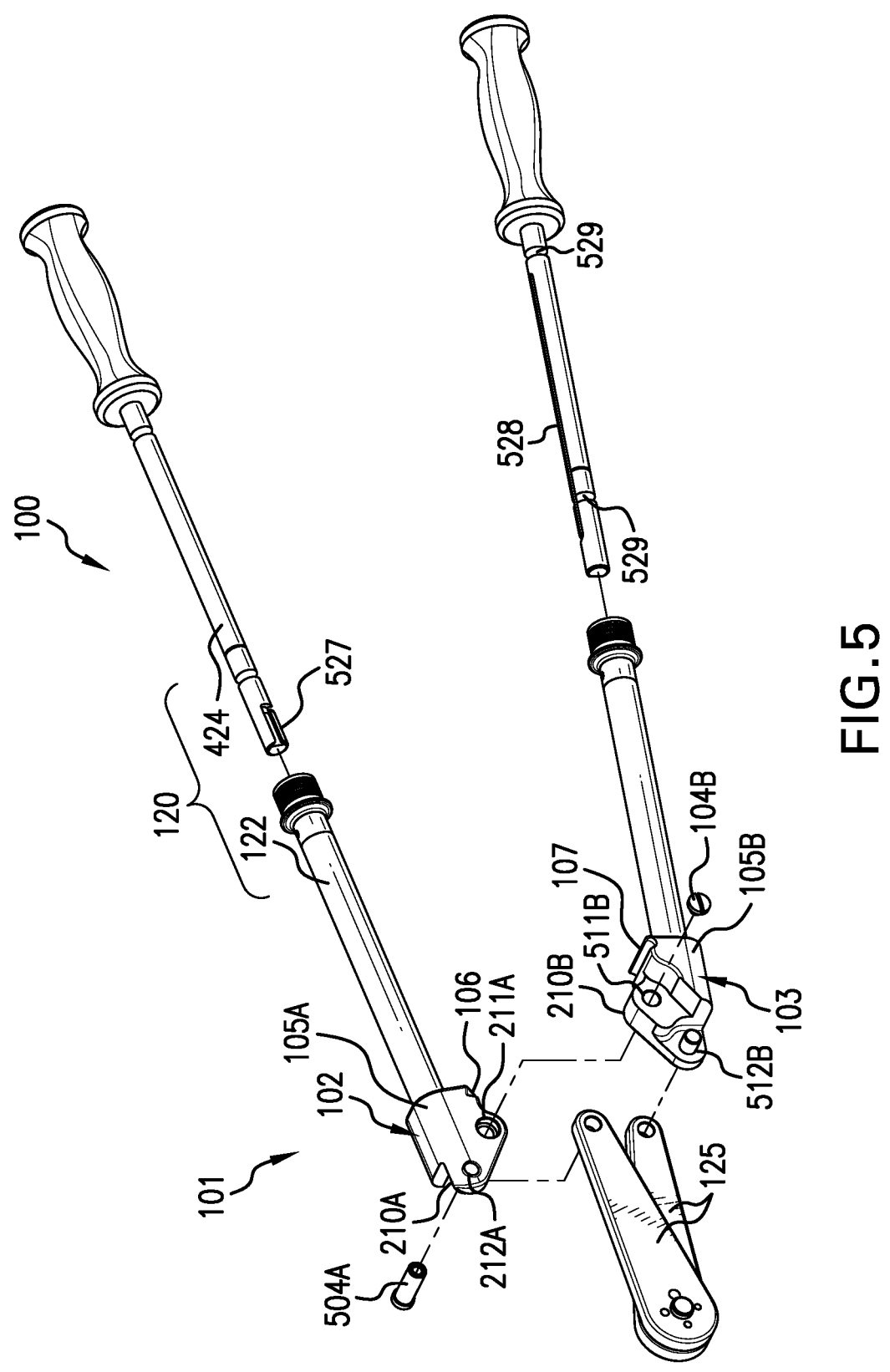
FIG. 5 is an exploded perspective view of the surgical rod cutter-bender assembly of FIG. 1, in accordance with an exemplary embodiment of the present invention.

Referring now to FIG. 2, there is shown a perspective view of surgical rod cutter-bender assembly 100 of FIG. 1, with portions broken away. Thus, a close-up view of pivot block assembly 101 is shown. First portion 102 is shown to further include an extension 210A including a pivot hole 211A (through-hole), which can receive the pivot pin of fastener assembly 104 at least partially therein. Extension 210A is coupled with (for example, can be formed integral with) and extends beyond base 105A. Second portion 103 also includes an extension 210B which is coupled with (for example, can be formed integral with) and extends beyond base 105B. Extension 210B also includes a pivot hole 511B (FIG. 5). Extensions 210A, 210B, according to an exemplary embodiment of the present invention, are configured such that pivot axis 108 extends through pivot hole 211A and 511B. Extensions 210A, 210B further include holes 212A and 512B (FIG. 5) for coupling (such as pivotably) portions 102, 103 with jaws 125, respectively, such as by way of any suitable fasteners, or the like.

Figure 3:
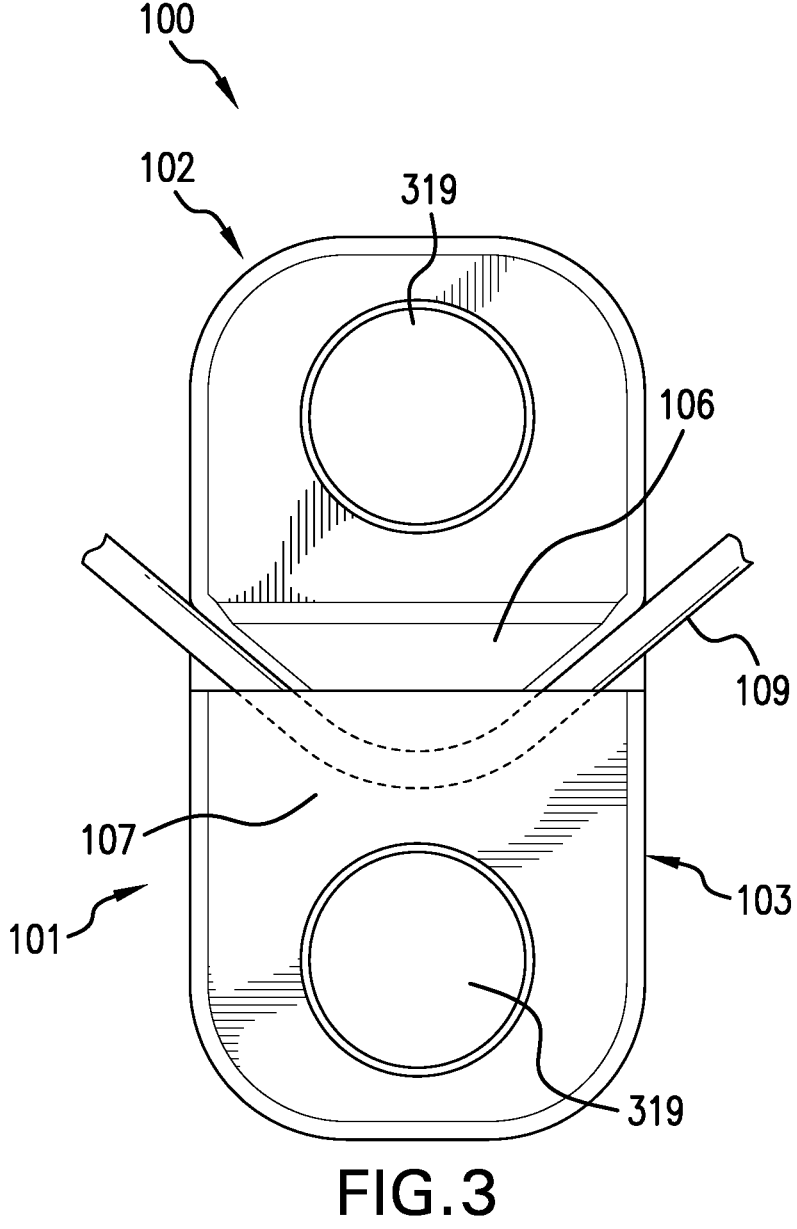
FIG. 3 is a schematic rear view of the surgical rod cutter-bender assembly of FIG. 1, with the surgical rod having been bent by the surgical rod cutter-bender assembly, in accordance with an exemplary embodiment of the present invention.

Referring now to FIG. 3, there is shown schematically a rear view (looking proximal to distal) of surgical rod cutter-bender assembly 100, with portions broken away, and with surgical rod 109 having been bent by surgical rod cutter-bender assembly 100. First portion 102 has been pivoted downwardly toward second portion 103, has contacted rod 109, and pushed rod 109, by way of protrusion 106, downwardly into a bottom of recess 107. Thus, recess 107 is configured for receiving at least a portion of surgical rod 109 therein when protrusion 106 pushes surgical rod 109 into recess 107 in order to bend surgical rod 109. In this way, according to an exemplary embodiment of the present invention, a three-point bend can be formed in rod 109. The relative dimensions of portions 102, 103 shown in FIG. 3 can vary, as compared to what is shown schematically in FIG. 3. Further, each portion 102, 103 is shown to include a respective hole 319 for receiving a respective shaft 122 therein.

Figure 4:
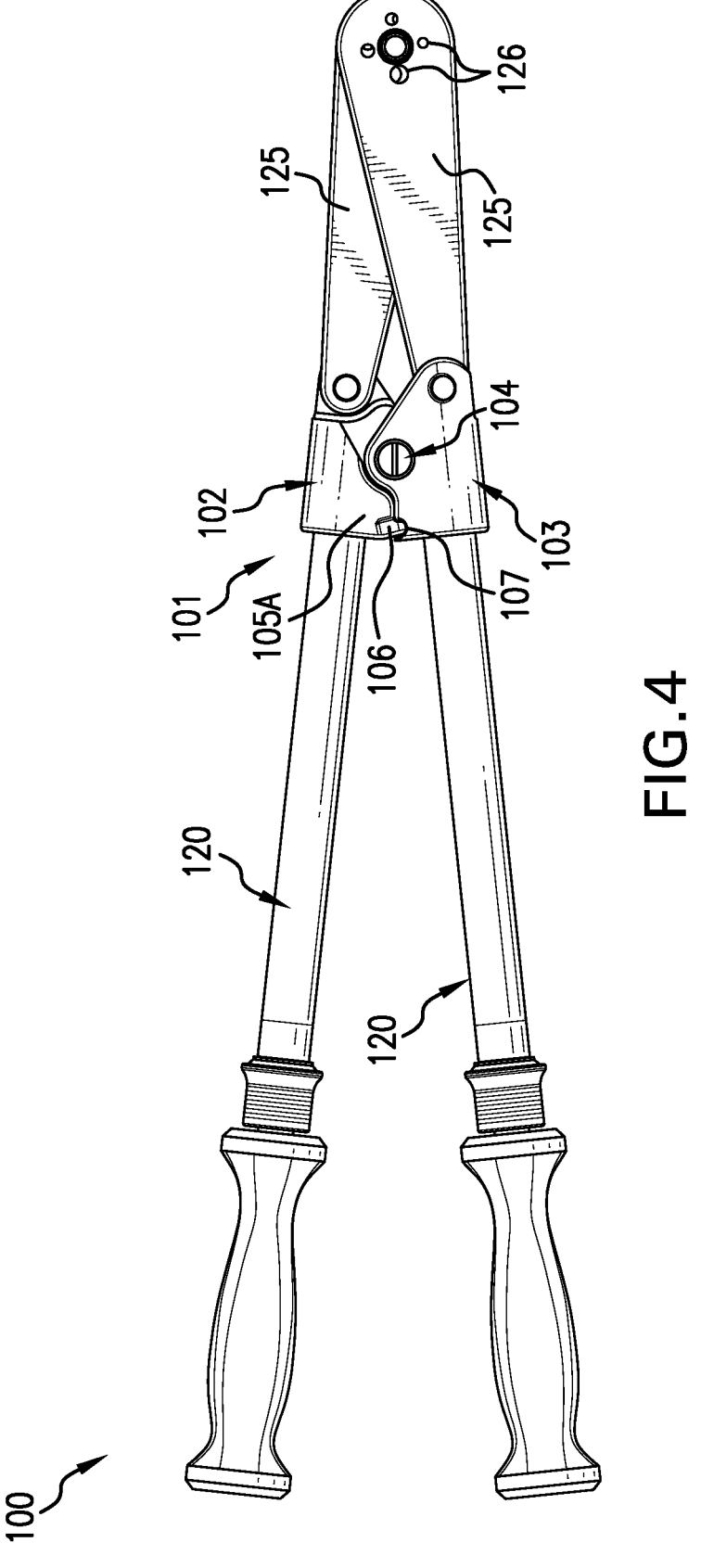
FIG. 4 is a side view of the surgical rod cutter-bender assembly of FIG. 1, with the surgical rod cutter-bender assembly shown in a closed position, though lacking the surgical rod, in accordance with an exemplary embodiment of the present invention.

Referring now to FIG. 4, there is shown a side view of surgical rod cutter-bender assembly 100, with handles 120 in a closed position relative to one another. Assembly 100 is shown to include pivot block assembly 101, handles 120, and jaws 125. Pivot block assembly 101 is shown to include first and second portions 102, 103, which respectively include protrusion 106 and recess 107. From this side view, it can readily be seen that protrusion is slightly angled inwardly; it can be appreciated that the protrusion can project from base 105A at any suitable angle, depending upon the specific design.

Referring now to FIG. 5, there is shown an exploded perspective view of surgical rod cutter-bender assembly 100. Assembly 100 is shown to include handles 120, pivot block assembly 101, and jaws 125. Each handle 120, as shown, can be an assembly, wherein handle 120 includes shaft 122 and shaft 424, which is configured for being telescoping within shaft 122, so as to increase or decrease the mechanical advantage, according to what suits the surgeon. Shaft 424 can lock with shaft 122 by way of, at least in part, a bayonet slot 527 in each shaft 424, a longitudinally extending longitudinal sliding slot 528 in each shaft 424, two grooves 529 in each shaft 424 (one groove 529 located proximally on shaft 424 and the other groove 529 located distally on shaft 424), and a ball (not shown) on an interior surface of shaft 122 to engage selectively in slots 527, 528, and grooves 529; for instance, the ball can lock into proximal groove 529 to hold shaft 424 in a retracted or collapsed position, or, alternatively, into the distal groove 529 to hold shaft 424 in an extended position. Each shaft 122 is connected to a respective portion 102, 103. Pivot block assembly 101 is shown to include first and second portions 102, 103, with, respectively, bases 105A, 105B and extensions 210A, 210B. Bases 105A, 105B include protrusion 106 and recess 107, respectively. Extensions 210A, 210B include pivot holes 211A, 511B with respect to pivot axis 108 and holes 212A, 512B for jaws 125. Though not labeled, holes 212A, 512B, as well as corresponding holes in jaws 125 can receive a respective pivot pin (with grease having been applied to these pivot pins) connecting corresponding structure to one another. Further, fastener assembly 104 includes pivot pin 504A and cap/screw 104B (which can be threadably received by pin 504A), pivot pin 504A and/or cap 104B being received within holes 211A, 511B to pivotably connect portions 102, 103 together (and cap/screw 104B being threadably received in an end of pivot pin 504A, with thread locking adhesive having been applied to threads of cap/screw 104B).

Figure 6:
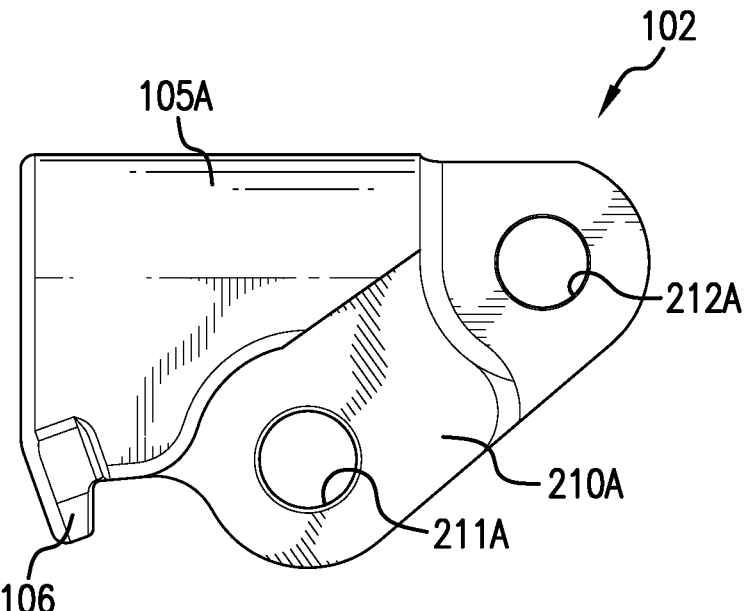
FIG. 6 is a side view of the first portion of the pivot block assembly of the surgical rod cutter-bender assembly of FIG. 1, in accordance with an exemplary embodiment of the present invention.

Referring now to FIG. 6, there is shown a side view of first portion 102. First portion 102 is shown to include base 105A, extension 210A, pivot hole 211A, hole 212A for a respective jaw 125, and protrusion 106. The proximal side of portion 102 is on the left side in FIG. 6.

Figure 7:
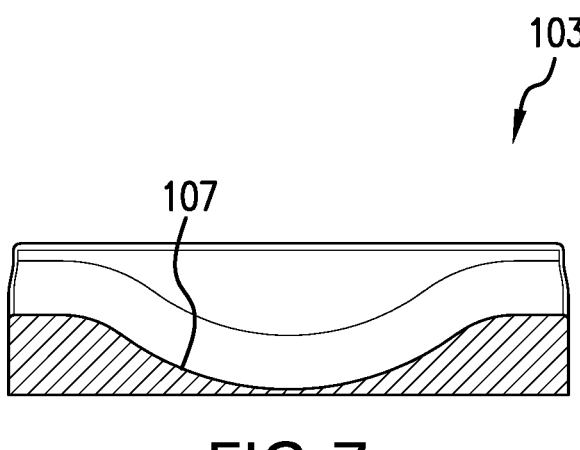
FIG. 7 is a cross-sectional view of the second portion of the pivot block assembly of the surgical rod cutter-bender assembly of FIG. 1, with portions broken away, the cross-section being taken along line 7-7 in FIG. 2, in accordance with an exemplary embodiment of the present invention.

Referring now to FIG. 7, there is shown a cross-sectional view of second portion 103, taken along line 7-7 in FIG. 2. Recess 107, as indicated, can have a surface that substantially mates with the shape of protrusion 106, when protrusion 106 rests in recess 107 without surgical rod 109 therebetween.

Figure 8:
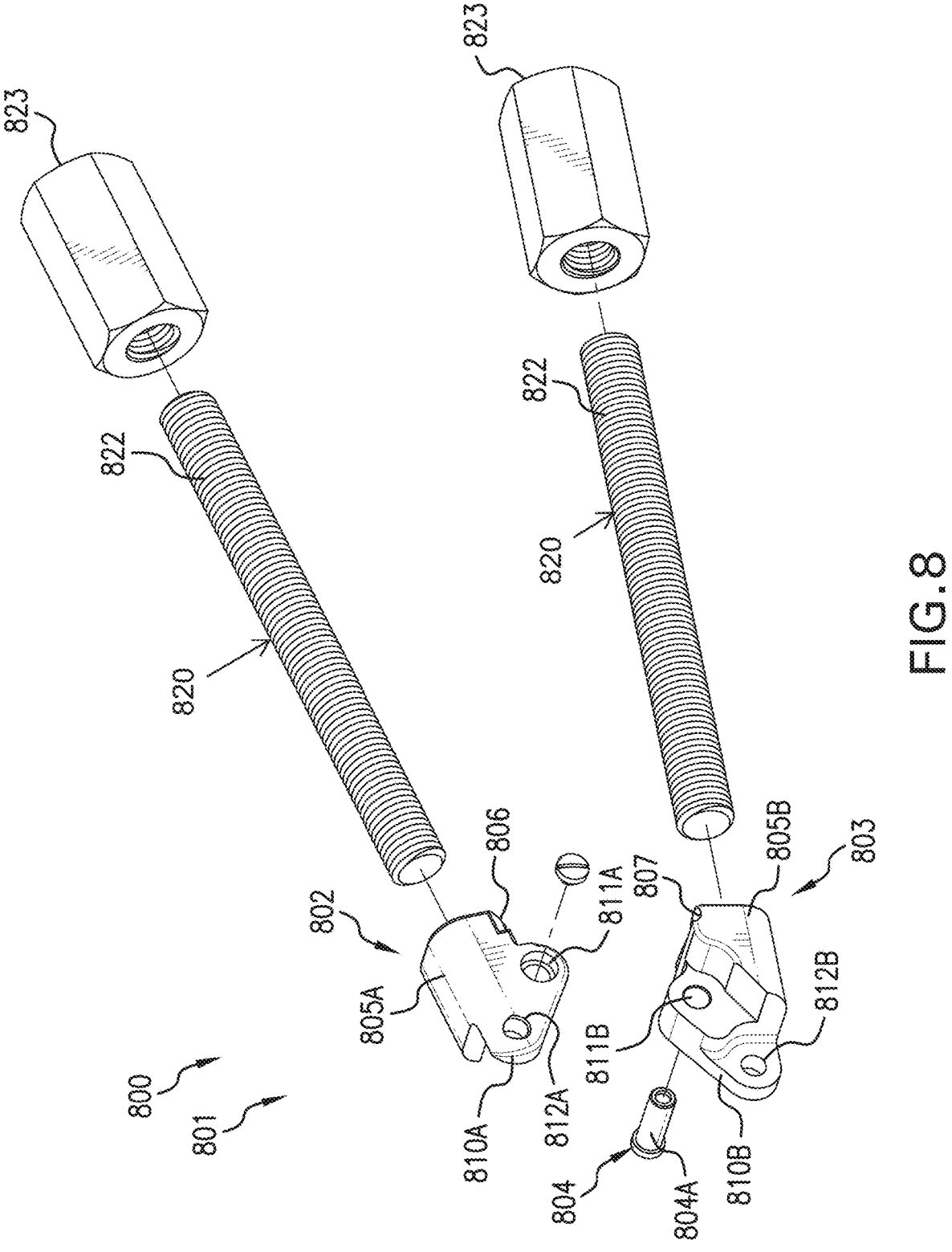
FIG. 8 is an exploded, perspective view of another exemplary embodiment of the surgical rod cutter-bender assembly, with portions broken away, the surgical rod cutter-bender assembly including a pivot block assembly including a first portion and a second portion, in accordance with an exemplary embodiment of the present invention.

Referring now to FIG. 8, there is shown an exploded perspective view of another embodiment of the surgical rod cutter-bender assembly, in accordance with an exemplary embodiment of the present invention. All prior reference numbers with respect to surgical rod cutter-bender assembly 100 are increased by a multiple of 100 and are substantially similar to the structures and function described and shown with respect to FIGS. 1-7, unless otherwise shown and/or described differently. Thus, surgical rod cutter-bender assembly 100 is labeled as 800 in FIG. 8. Surgical rod cutter-bender assembly 800 includes pivot block assembly 801, at least one handle 820, and a plurality of jaws (not shown in FIG. 8, but substantially similar to jaws 125) attached to pivot block assembly 801. Upper and lower handles 820 and their respective grippers 823 are shown. Further, pivot block assembly 801 includes first and second portions 802, 803, which include bases 805A, 805B and extensions 810A, 810B, respectively. Extensions 810A, 810B include holes 811A, 811B, 812A, 812B, respectively, and pivot pin 804A of fastener assembly 804 is received within holes 811A, 811B to pivotably connect portions 802, 803 together. The primary differences between the embodiment of FIGS. 1-7 and the embodiment shown in FIGS. 8-11 concern handles 120/820, protrusions 106/806, and recesses 107, 807. Regarding handles 120/820, shaft 822 of each handle 820 is threadably received by gripper 823 and portions 802, 803. Regarding protrusions 106/806, protrusion 806 is substantially vertical (FIG. 9), whereas protrusion 106 is angled inwardly (FIG. 6). Regarding recesses 107/807, an upward curvature leads to recess 807 (such an upward curvature is lacking with respect to recess 107, and recess 807 is shown to include a dip 813 in its exterior wall (FIG. 11)(the exterior wall of recess 107 lacks such a dip). Thus, during assembly, shafts 822 can be threaded into grippers 823 and into portions 802, 803 (with the flats of the hexagonal cross-section of grippers 823 being aligned). Pivot holes 811A, 811B are aligned so that pivot pin 804A can be inserted therein. Further, screw 804B (which can be deemed to be a part of fastener assembly 804) can be screwed by ways of threads into pin 804A.

Figure 9:
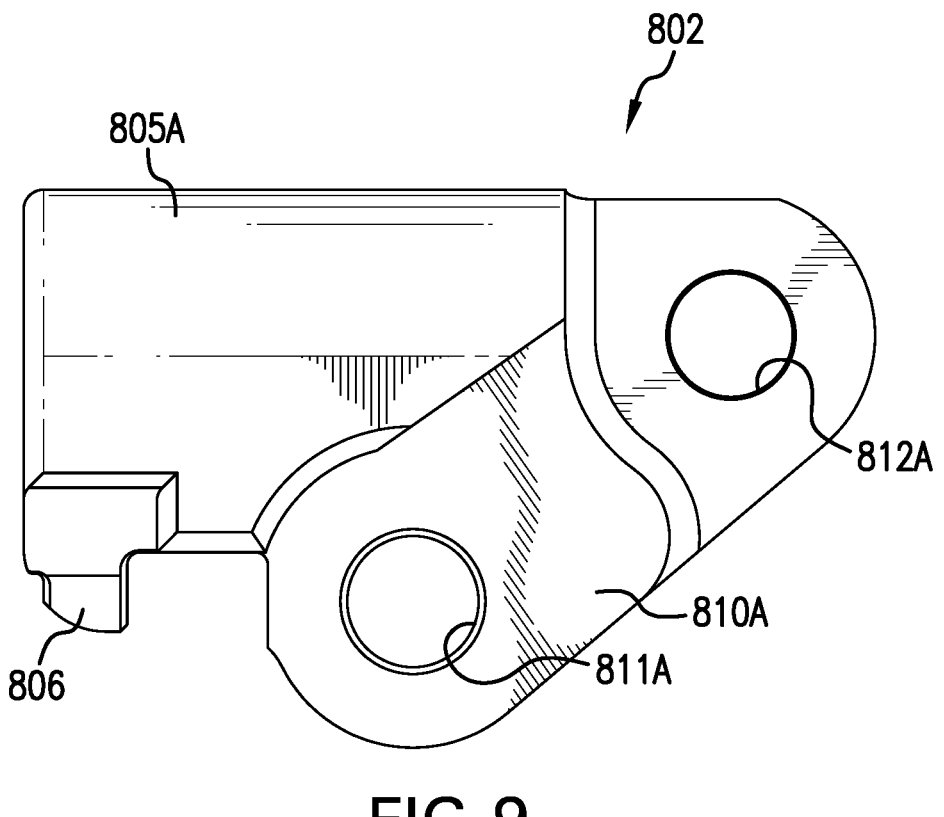
FIG. 9 is a side view of the first portion of the pivot block assembly of the surgical rod cutter-bender assembly of FIG. 8, in accordance with an exemplary embodiment of the present invention.

Referring now to FIG. 9, there is shown a side view of first portion 802. First portion 802 is shown to include base 805A, extension 810A, pivot hole 811A, hole 812A for a respective jaw 125, and protrusion 806. The proximal side of portion 802 is on the left side in FIG. 9. As can be seen, protrusion 906 is offset right (distally) slightly from a left side wall of base 805A.

Figures 10, 11:
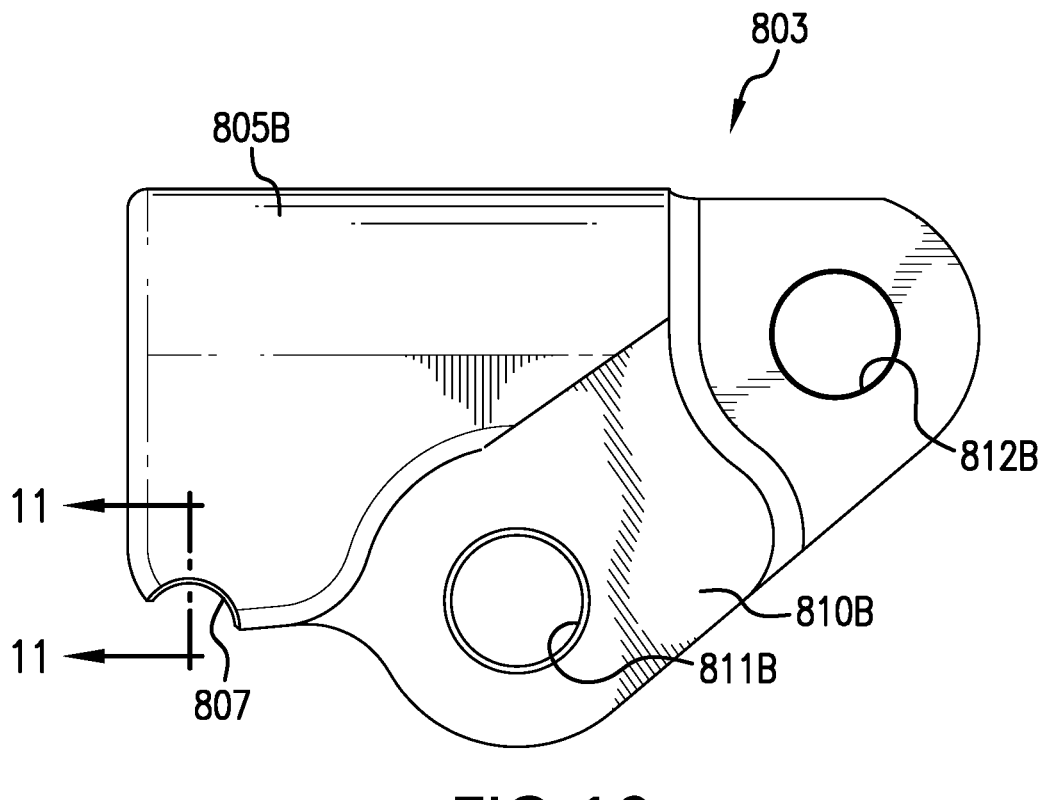
FIG. 10 is a side view of the second portion of the pivot block assembly of the surgical rod cutter-bender assembly of FIG. 8, in accordance with an exemplary embodiment of the present invention.
FIG. 11 is a cross-sectional view of the second portion of FIG. 8, taken along line 11-11 in FIG. 10, in accordance with an exemplary embodiment of the present invention.

Referring now to FIG. 10, there is shown a side view of second portion 803. Second portion 803 is shown to include base 805B, extension 810B, pivot hole 811B, hole 812B for a respective jaw 125, and recess 807.

Referring now to FIG. 11, there is shown a cross-sectional view of second portion 803, taken along line 11-11 in FIG. 10. Recess 807 is shown to include a dip 813 in its exterior wall.

Figure 12:
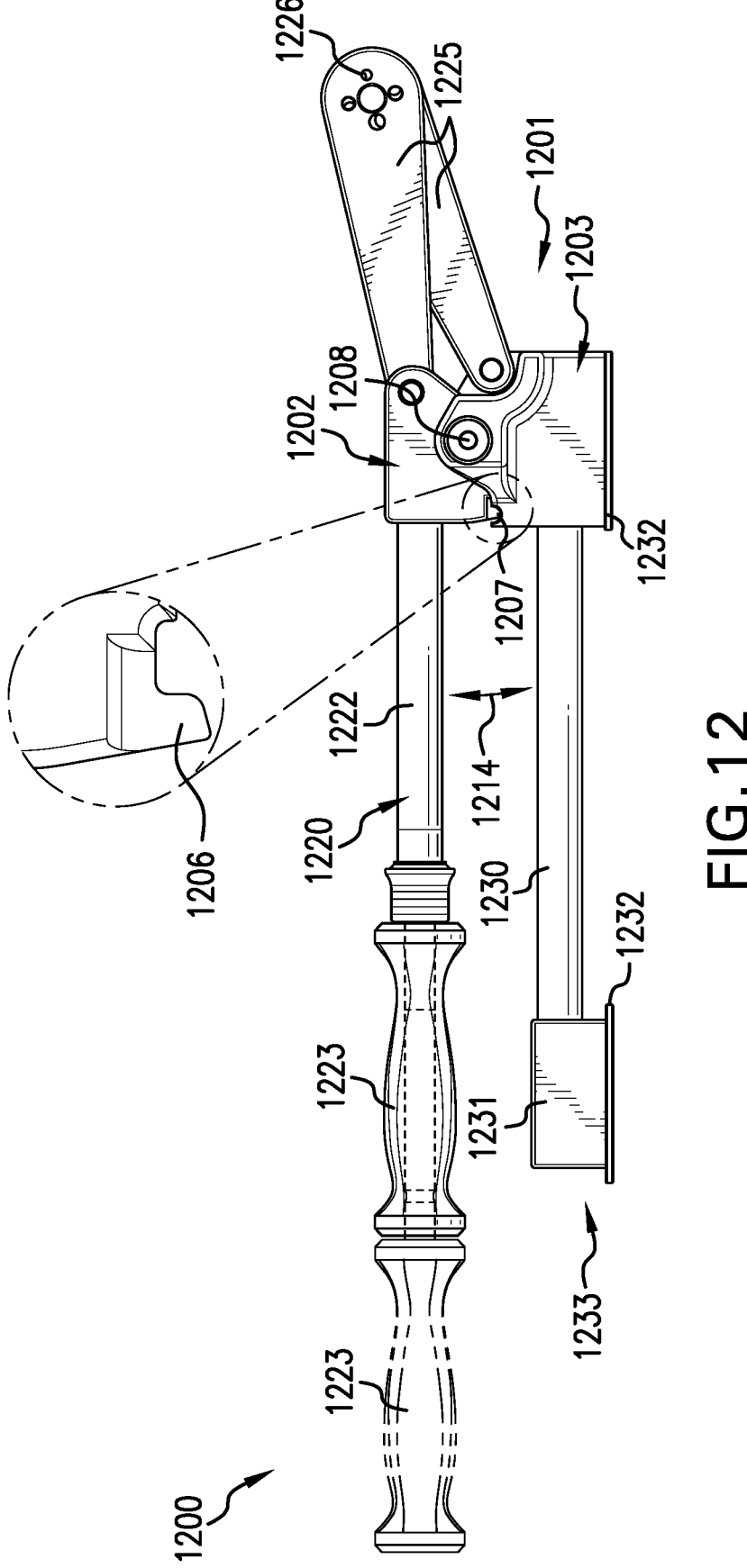
FIG. 12 is a perspective view of yet another exemplary embodiment of the surgical rod cutter-bender assembly, the surgical rod cutter-bender assembly including a pivot block assembly including a first portion and a second portion, in accordance with an exemplary embodiment of the present invention.

Referring now to FIG. 12, there is shown a perspective view of yet another exemplary embodiment of the surgical rod cutter-bender assembly, in accordance with an exemplary embodiment of the present invention. All prior reference numbers with respect to surgical rod cutter-bender assembly 100 are increased by a multiple of 100 and are substantially similar to the structures and function described and shown with respect to FIGS. 1-7, unless otherwise shown and/or described differently. Thus, surgical rod cutter-bender assembly 100 is labeled as 1200 in FIG. 12, with FIGS. 12-15 showing an embodiment of a table-top configuration for assembly 1200. Surgical rod cutter-bender assembly 1200 includes jaws 1225, one handle 1220, a bottom assembly 1233, and pivot block assembly 1201. Jaws 1225 are pivotably attached to pivot block assembly 1201. Similar to what is shown and described with respect to handle 120 (FIG. 5), handle 1220 can be lengthened by way of a telescoping assembly to an extended position in order to provide a greater mechanical advantage (as shown in broken lines in FIG. 12), or shortened to a retracted position (as shown in solid lines in FIG. 12). Further, handle 1220, which includes gripper 1223) is configured for selectively pivoting up and down, that is, away from and towards bottom assembly 1233, as indicated by bi-directional arrow 1214. Bottom assembly 1233 includes bottom arm 1230, base 1231, and two feet 1232. Arm 1230 is affixed to and extends between pivot block assembly 1201 (more specifically, second portion 1203 thereof) and base 1231, and is connected to portion 1203 and base 1231 in any suitable manner. Further, a respective foot 1232 is connected to a bottom side of second portion 1203 and a bottom side of base 123. Each foot 1232 is configured for being mounted and thus secured to a top surface of a table (not shown). Pivot block assembly 1201 includes first portion 1202 and second portion 1203, which are pivotably connected to one another and thus are configured for pivoting about pivot axis 1208 away from and toward one another according to bi-directional arrow 1214. First portion 1202 includes protrusion 1206, and second portion 1203 includes recess 1207.

Figure 13:
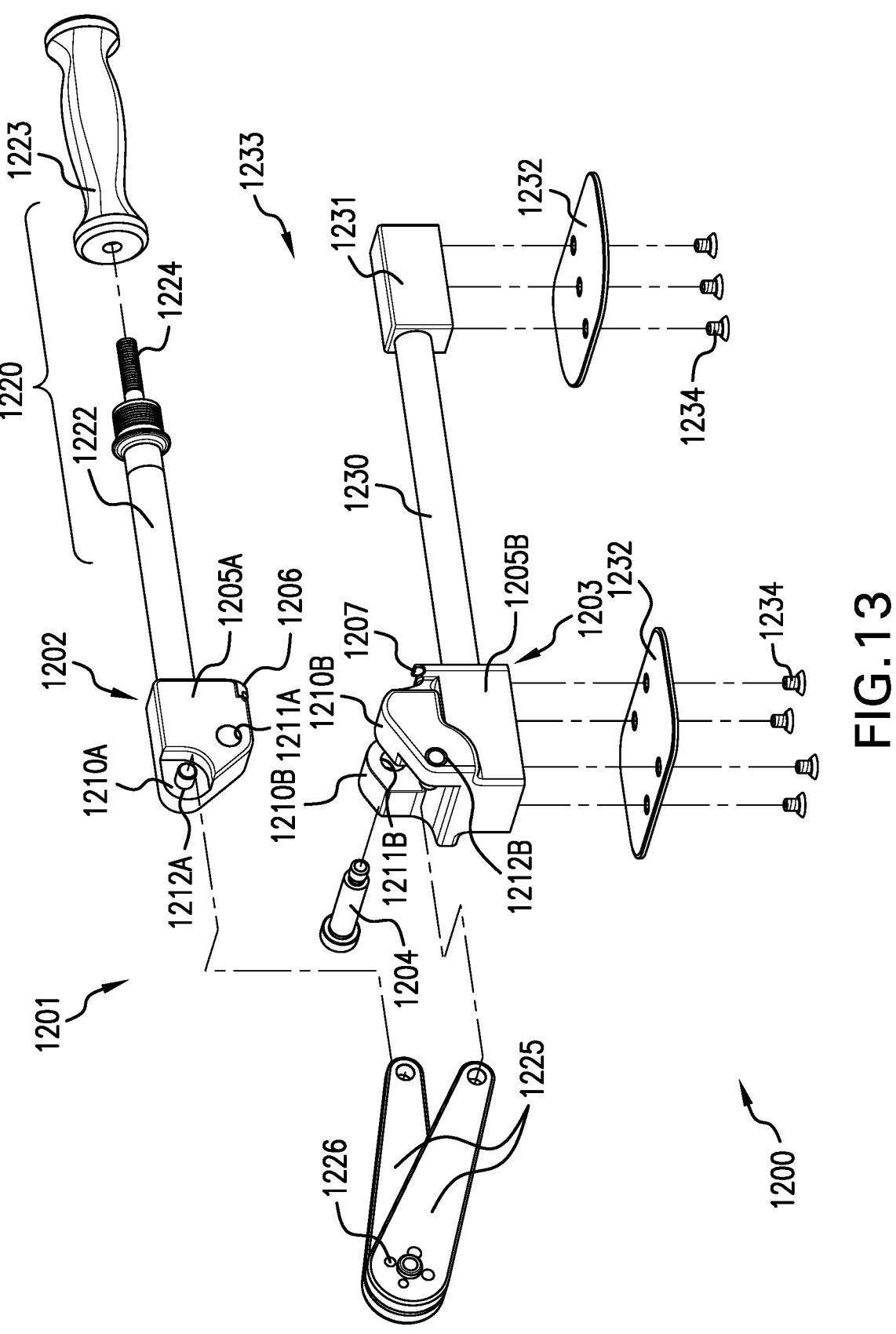
FIG. 13 is an exploded, perspective view of the surgical rod cutter-bender assembly of FIG. 12, in accordance with an exemplary embodiment of the present invention.

Referring now to FIG. 13, there is shown an exploded perspective view of surgical rod cutter-bender assembly 1200. Assembly 1200 is shown to include includes jaws 1225, one handle 1220, a bottom assembly 1233, and pivot block assembly 1201. Jaws 1225 connect with first and second portions 1202, 1203 respectively by way of pivot pins, for example, in holes 1212A, 1212B of portions 1202, 1203, respectively (such pivot pins are shown in FIG. 13 in holes 1212A, 1212B). Shaft 1222 of handle 1220 (which also includes shaft 1224) can connect with gripper 1223 in any suitable manner, such as by way of a threaded connection, and can connect with a hole in first portion 1202 in any suitable manner, such as a threaded connection, an interference fit, welding, and/or the like. Arm 1230 connects at respective ends of arm 1230 with base 1231 and second portion 1203 in any suitable manner, such as a threaded connection, an interference fit, welding, and/or the like. Feet 1232, formed for example as a metal plate, connects respectively with base 1231 and second portion 1203 by way of threaded fasteners 1234 of bottom assembly 1233, fasteners 1234 extending through holes in feet 1232 and into base 1231 and second portion 1203. First portion 1202 and second portion 1203 of pivot block assembly 1201 include, respectively base 1205A, 1205B, extensions 1210A, 1210B, pivot holes 1211A, 1211B, and jaw pivot holes 1212A, 1212B. Second portion includes two upstanding extensions 1210B which form a space 1218 therebetween (FIG. 15), space 1218 receiving first portion 1202 therebetween, with holes 1211A, 1211B aligned with one another so as to receive fastener 1204 therein. Each upstanding extension 1210B can include a respective hole 1211B, one hole 1211B in one upstanding extension 1210B being a through-hole (visible in FIG. 13), the other hole 1211B in the other upstanding extension 1210B optionally being a blind hole (visible in FIG. 15), which can be threaded, so as to threadably receive a threaded end of fastener 1204 therein, which can be a screw 1204 or bolt 1204). First and second portions 1202, 1203 include protrusion 1206 and recess 1207, respectively. The detail bubble shown in FIG. 12 shows only a portion of top portion 1202, including protrusion 1206.

Figure 14:
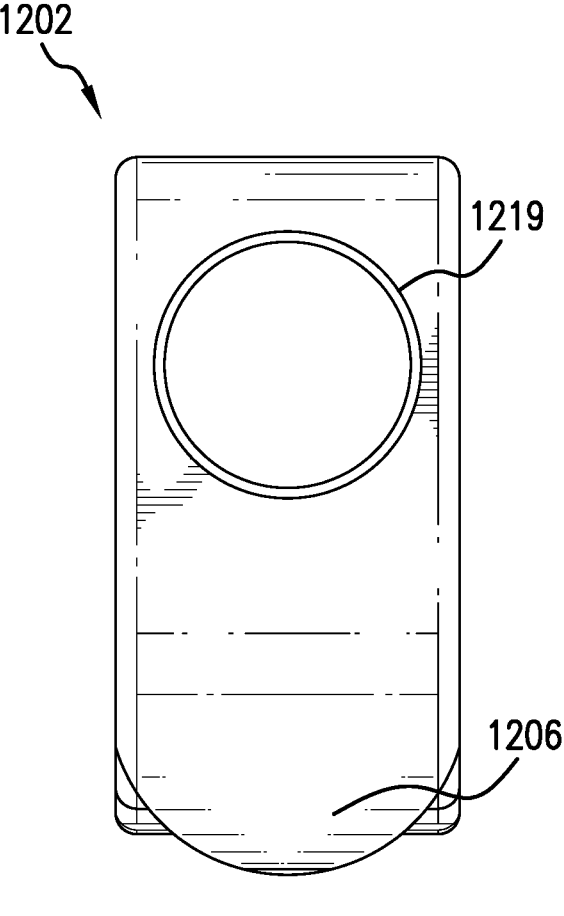
FIG. 14 is a rear view of the first portion of the surgical rod cutter-bender assembly of FIG. 12, in accordance with an exemplary embodiment of the present invention.

Referring now to FIG. 14, there is shown a rear view of first portion 1202 of surgical rod cutter-bender assembly 1200. First portion 1202 is shown to include protrusion 1206 and hole 1219 for receiving an end of shaft 1222.

Figure 15:
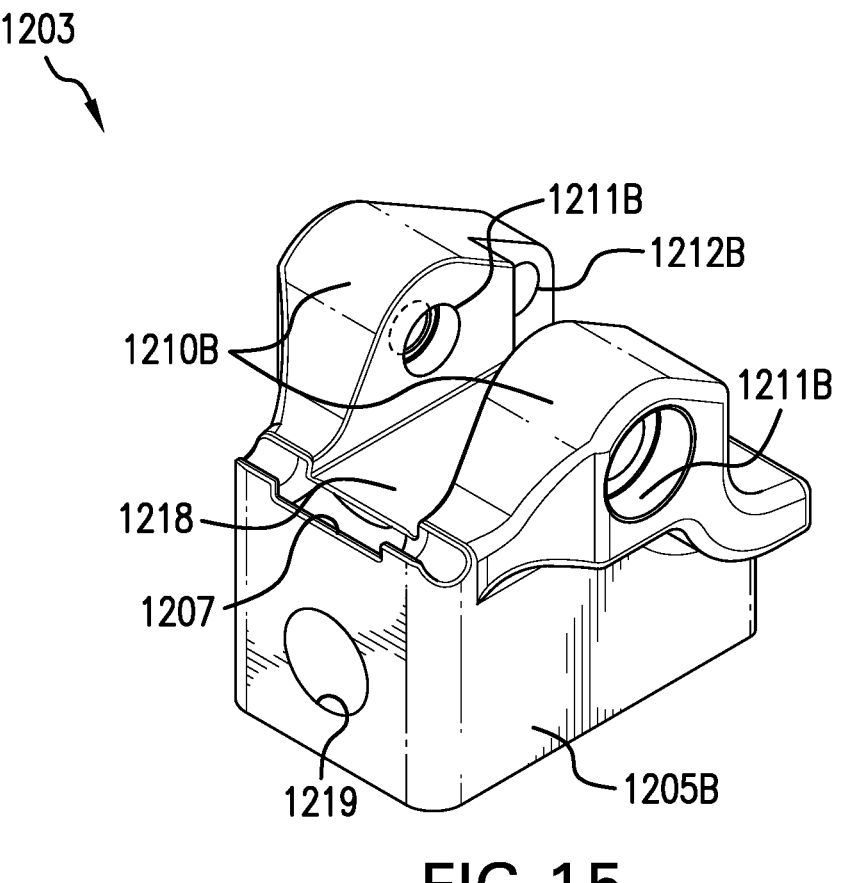
FIG. 15 is a rear, perspective view of the second portion of the surgical rod cutter-bender assembly, in accordance with an exemplary embodiment of the present invention.

Referring now to FIG. 15, there is shown a rear, perspective view of second portion 1203 of surgical rod cutter-bender assembly 1200. Second portion 1203 is shown to include base 1205B including a hole (a blind hole) 1219 therein for receiving arm 1230 therein, recess 1207 in base 1205B, and two upstanding extensions 1210B with space 1218 therebetween. Each extension 1210B includes a respective pivot hole 1211B, 1211B, and one extension 1210B includes jaw pivot hole 1212B.

In use, assembly 100, 800, 1200 can selectively cut surgical rods 109, and selectively bend surgical rods 109. With regard to cutting, when the user wishes to cut rod 109, the user raises the handle 1220 (tabletop configuration) or separates the two handles 120, 820 (handheld configuration) to allow for insertion of rod 109 selectively into one of cutting holes 126, 1226 at the distal end of assembly 100, 800, 1200, wherein as a result rod 109 is placed between two cutting jaws 125, 1225. When the user brings handle 1220 down (tabletop configuration) or brings handles 120, 820 together (handheld configuration) relative to the pivot axis 108, 1208 surgical rod 109 is sheared. With regard to bending, when the user wishes to bend rod 109, handles 120, 820 are spread apart and closed (handheld configuration), or handle 1220 is moved away from (opened) and moved towards (closed) and bottom assembly 1233. However, rod 109 is not placed into any of cutting holes 126, 1226 but is placed atop recess 107, 807, 1207 of female portion 103, 803, 1203 of pivot block assembly 101, 801, 1201 in an interior of pivot block assembly 101, 801, 1201 near the pivot area. As the user brings handle 1220 down (tabletop configuration) or handles 120, 820 together (handheld configuration), protrusion 106, 806, 1206 of male portion 102, 802, 1202 of pivot block assembly 101, 801, 1201 contacts and pushes a portion of rod 109 into the bottom of recess 107, 807, 1207. Thus, the bending action is performed in the same manner as the cutting action, with the exception that rod 109 is placed atop (or above) recess 107, 807, 1207 on the interior portion of pivot block assembly 101, 801, 1201 and thus in a central joint of assembly 100, 800, 1200. Further, the extended length of handle(s) 120, 820, 1220 allows less required user applied load when cutting or bending and gives the user more control when cutting or bending. Optionally, handle(s) 120, 820, 1220 can be telescoping to selectively provide even greater length and thus greater mechanical advantage. In manufacturing assembly 100, 800, 1200, any suitable manufacturing methods can be used, for example and not by way of limitation, milling. Custom tooling can be used to make protrusion 106, 806, 1206 and recess 107, 807, 1207. Further, pivot block assembly 101, 801, 1201 can be made, alternative to milling, by way of casting or forging. However, surgical rod cutter-bender assembly 100, 800, 1200, or any part thereof, can be made using any suitable method of manufacture, regardless of whether such method is mentioned herein.

Figure 16:
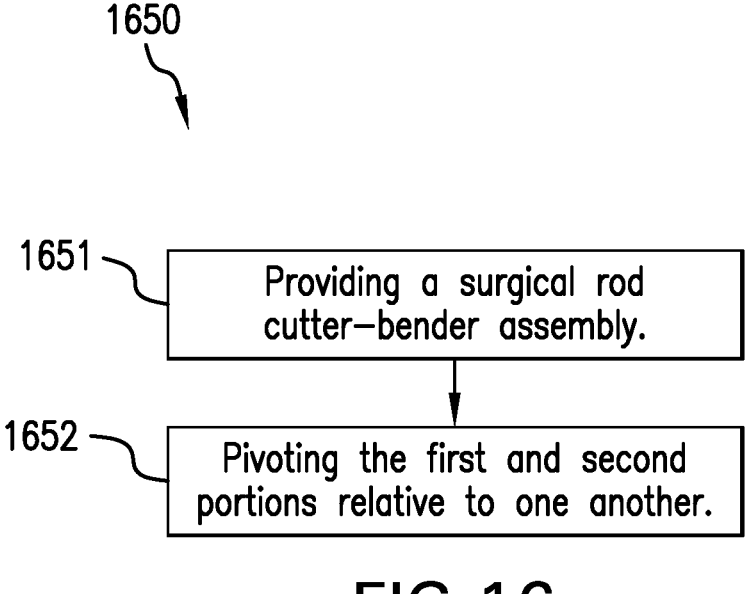
FIG. 16 is a flow diagram showing a method of using of using the surgical rod cutter-bender assembly, in accordance with an exemplary embodiment of the present invention.

Referring now to FIG. 16, there is shown a flow diagram showing a method 1650 of using surgical rod cutter-bender assembly 100, 800, 1200. Method 1650 includes the steps of: providing 1651 that surgical rod cutter-bender assembly 100, 800, 1600 includes a first portion 102, 802, 1202 and a second portion 103, 803, 1203, first portion 102, 802, 1202 including a protrusion 106, 806, 1206, second portion 103, 803, 1203 including a recess 107, 807, 1207 associated with the protrusion 106, 806, 1206, first portion 102, 802, 1202 and second portion 103, 803, 1203 together defining a pivot axis 108, 1208; and pivoting 1652 first portion 102, 802, 1202 and second portion 103, 803, 1203 relative to one another about pivot axis 108, 1208. Surgical rod cutter-bender assembly 100, 800, 1200 can further include a pivot block assembly 101, 801, 1201 including first portion 102, 802, 1202 and second portion 103, 803, 1203 which are coupled with one another, protrusion 106, 806, 1206 and recess 107, 807, 1207 being positioned proximally relative to 108, 1208 pivot axis. Surgical rod cutter-bender assembly 100, 800, 1200 can further include a plurality of jaws 125, 1225 coupled with pivot block assembly 101, 801, 1201 and configured for cutting a surgical rod 109 including stainless steel, titanium, cobalt chromium, and/or a polymer. Jaws 125, 1225 can be positioned distally relative to pivot axis 108, 1208. Recess 107, 807, 1207 can be configured for receiving at least a portion of surgical rod 109 therein when protrusion 106, 806, 1206 pushes surgical rod 109 into recess 107, 807, 1207 in order to bend surgical rod 109. Surgical rod cutter-bender assembly 100, 800, 1200 can further include at least one handle 120, 820, 1220 coupled with first portion 102, 802, 1202 or second portion 103, 803,

1203. Protrusion 106, 806, 1206 and recess 107, 807, 1207 can be substantially parallel relative to pivot axis 108, 1208. First portion 102, 802, 1202 can include a base 105A, 805A, 1205A and an extension 210A, 810A, 1210A including a first pivot hole 211A, 811A, 1211A. Surgical rod cutter-bender assembly 100, 800, 1200 can include a handheld configuration (FIGS. 1-11) or a tabletop configuration (FIGS. 12-15). Second portion 103, 803, 1203 can include a base 105B, 805B, 1205B and an extension 210B, 810B, 1210B including a second pivot hole 511B, pivot axis 108, 1208 extending through first pivot hole 211A, 811A, 1211A and second pivot hole 511B, 811B, 1211B.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical rod cutter-bender assembly, comprising:
 a first portion including a protrusion; and
 a second portion including a recess associated with the protrusion, the first portion and the second portion together defining a pivot axis such that the first portion and the second portion are configured for pivoting relative to one another about the pivot axis, the protrusion and the recess being positioned proximally relative to the pivot axis when the surgical rod cutter-bender assembly is in a closed position, the protrusion including a first lateral side, a second lateral side opposing the first lateral side, and a middle section positioned between the first lateral side and the second lateral side, the middle section extending lower than the first lateral side and the second lateral side when the surgical rod cutter-bender assembly is in the closed position, the first lateral side and the second lateral side being spaced apart transversely from one another and thus along a transverse axis that is parallel to the pivot axis.

2. The surgical rod cutter-bender assembly of claim 1, further comprising a pivot block assembly including the first portion and the second portion which are coupled with one another.

3. The surgical rod cutter-bender assembly of claim 2, further comprising a plurality of jaws coupled with the pivot block assembly and configured for cutting a surgical rod including stainless steel, titanium, or cobalt chromium.

4. The surgical rod cutter-bender assembly of claim 3, wherein the plurality of jaws are positioned distally relative to the pivot axis.

5. The surgical rod cutter-bender assembly of claim 4, wherein the recess is configured for receiving at least a portion of the surgical rod therein when the protrusion pushes the surgical rod into the recess in order to bend the surgical rod.

6. The surgical rod cutter-bender assembly of claim 5, further comprising at least one handle coupled with the first portion or the second portion.

7. The surgical rod cutter-bender assembly of claim 6, wherein the protrusion and the recess are substantially parallel relative to the pivot axis.

8. The surgical rod cutter-bender assembly of claim 7, wherein the first portion includes a base and an extension including a first pivot hole, the surgical rod cutter-bender assembly including a handheld configuration or a tabletop configuration.

9. The surgical rod cutter-bender assembly of claim 7, wherein each one of the plurality of jaws includes respectively a distal end, the plurality of jaws being coupled with one another at the distal end of each respective one of the plurality of jaws.

10. The surgical rod cutter-bender assembly of claim 8, wherein the second portion includes a base and an extension including a second pivot hole, the pivot axis extending through the first pivot hole and the second pivot hole.

11. The surgical rod cutter-bender assembly of claim 1, wherein the surgical rod cutter-bender assembly further includes a pivot block assembly and a plurality of jaws, the pivot block assembly including the first portion and the second portion which are coupled with one another, the plurality of jaws being coupled with the pivot block assembly and configured for cutting a surgical rod, wherein the plurality of jaws are positioned distally relative to the pivot axis, wherein each one of the plurality of jaws includes respectively a distal end, the plurality of jaws being coupled with one another at the distal end of each respective one of the plurality of jaws.

* * * * *